US010017789B2

(12) United States Patent
Atiyeh et al.

(10) Patent No.: US 10,017,789 B2
(45) Date of Patent: Jul. 10, 2018

(54) SYSTEM AND METHOD FOR FEEDBACK CONTROL OF GAS SUPPLY FOR ETHANOL PRODUCTION VIA SYNGAS FERMENTATION USING PH AS A KEY CONTROL INDICATOR

(71) Applicant: The Board of Regents for Oklahoma State University, Stillwater, OK (US)

(72) Inventors: Hasan K. Atiyeh, Stillwater, OK (US); John Randall Phillips, Stillwater, OK (US); Raymond L. Huhnke, Stillwater, OK (US)

(73) Assignee: The Board Of Regents For Oklahoma State University, Stillwater, OK (US)

( * ) Notice: Subject to any disclaimer, the term of this patent is extended or adjusted under 35 U.S.C. 154(b) by 64 days.

(21) Appl. No.: 15/080,875

(22) Filed: Mar. 25, 2016

(65) Prior Publication Data
US 2016/0281114 A1 Sep. 29, 2016

Related U.S. Application Data

(60) Provisional application No. 62/138,080, filed on Mar. 25, 2015.

(51) Int. Cl.
*C12P 7/06* (2006.01)
*C12M 1/34* (2006.01)
*C12M 1/00* (2006.01)
*C12M 1/06* (2006.01)

(52) U.S. Cl.
CPC ............ *C12P 7/06* (2013.01); *C12M 21/12* (2013.01); *C12M 27/02* (2013.01); *C12M 41/26* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 4,680,267 | A * | 7/1987 | Eppstein | C12M 41/26 435/286.6 |
| 7,285,402 | B2 * | 10/2007 | Gaddy | C12P 7/065 435/140 |
| 9,617,566 | B2 | 4/2017 | Collet et al. | |
| 2007/0275447 | A1 * | 11/2007 | Lewis | C12P 7/06 435/161 |
| 2014/0011185 | A1 * | 1/2014 | Stroot | C12Q 3/00 435/3 |

FOREIGN PATENT DOCUMENTS

WO WO 2016077778 5/2016

OTHER PUBLICATIONS

Ahmed, et al., "Effects of Biomass-Generated Producer Gas Constituents on Cell Growth, Product Distribution and Hydrogenase Activity of Clostridium Carboxidivorans P7",2006, pp. 665-672, vol. 30, No. 7, Publisher: Biomass and Bioenergy, Published in: US.
Babu, et al., "Effect of the Reducing Agent Dithiothreitol on Ethanol and Acetic Acid Production by Clostridium Strain P11 Using Simulated Biomass-Based Syngas", Jan. 1, 2010, pp. 19-35, vol. 3, No. 2, Publisher: Biological Engineering, Published in: US.
Cheng, Li-Kun, et al., "Strategy FPR pH Control and pH Feedback-Controlled Substrate Feeding for High-Level Production of L-Tryptophan by *Escherichia coli*", Jan. 3, 2013, pp. 383-890, vol. 29, No. 5, Publisher: World Journal of Microbiology & Biotechnology, Published in: US.
Datar, Rohit, et al., "Fermentation of Biomass-Generated Producer Gas to Ethanol", "Biotechnology and Bioengineering", Apr. 15, 2004, pp. 587-594, vol. 86, No. 5, Publisher: Wiley Periodicals, Inc., Published in: US.
Drake, et al., "Old Acetogens, New Light", Nov. 25, 2008, pp. 100-108, vol. 1125, Publisher: Annals of the New York Academy of Sciences.
Gao, et al., "Development of Low Cost Medium for Ethanol Production From Syngas by Clostridium Ragadalei", 2013, pp. 508-515, vol. 147, Publisher: Bioresource Technology.
Kundiyana, et al., "Feasibility of Incorporating Cotton Seed Extract in Clostridium Strain P11 Fermentation Medium During Synthesis Gas Fermentation", Jul. 17, 2010, pp. 9673-9680, vol. 101, No. 2010, Publisher: Bioresource Technology 101, Published in: US.
Liou, S.-C Jack, et al., "*Clostidium carboxidivorans* SP. Nov. A Solvent-Producing Clostridium Isolated From an Agricultural Settling Lagoon, and Reclassification of the Acetogen Clostridium Scatologenes Strain SL1 as *Clostridium drakei* Sp. Nov.", May 27, 2005, pp. 2085-2091, vol. 55, Publisher: Int'l J. of Systematic and Evolutionary Microbiology, Published in: US.
Liu, K., et al., "Fermentive Production of Ethanol From Syngas Using Novel Moderately Alkaliphilic Strains of Alkalibaculum Bacchi", Oct. 1, 2011, pp. 336-341, vol. 104, Publisher: Bioresource Technology, Published in: US.
Liu et al., "Mixed Culture Syngas Fermentation and Conversion of Carboxylic Acids Into Alcohols", Nov. 15, 2013, Publisher: Bioresource Technology, Published in: US.
Maddipati, et al., "Ethanol Production From Syngas by Clostridium Strain P11 Using Corn 'Steep Liquor As a Nutrient Replacement to Yeast Extract", 2014, pp. 64946501, vol. 102, gumber 11, Publisher: Bioresource Technology, Published in: US abstract only.
Orgill, et al., "A Comparison of Mass Transfer Coefficients Between Trickel-Bed, Hollow Fiber Membrane and Stirred Tank Reactors", Apr. 1, 2013, pp. 340-346, vol. 133, Publisher: Bioresource Technology, Published in: US.

(Continued)

*Primary Examiner* — Emily A Cordas
(74) *Attorney, Agent, or Firm* — Crowe & Dunlevy; Terry L. Watt

(57) ABSTRACT

According to an embodiment, there is provided herein a system and method wherein knowledge of the syngas fermentation is combined with standard instrumentation to provide a stable control of gas supply to automatically poise the fermentation to provide both high conversion of CO and $H_2$, and high selectivity for production of ethanol. The control is based on an automatic feedback loop that corrects for operational imbalance and maintains a stable continuous fermentation required for commercial operation. In a further embodiment, feed of syngas to ethanol fermentation can be optimally controlled using the pH of the broth as the input variable for flow control of the gas. This concept will automatically maintain the correct supply of syngas to the fermentation, and provide stable operation at optimal rates.

13 Claims, 4 Drawing Sheets

(56) References Cited

OTHER PUBLICATIONS

Panneerselvam, et al., "Efects of Various Reducing Agents on Syngas Fermentation by Clostridium ragsdalei", pp. 135-144, vol. 2, No. 3, Publisher: Biological Engineering, Published in: US.

Phillips, et al., "Biological Production of Ethanol From Coal Synthesis Gas-Medium Development Studies", 1993, pp. 559-571, vol. 39, Publisher: Applied Biochemistry and Applied, Published in: US.

Phillips, et al., "Synthesis Gas As Substrate for the Biological Production of Fuels and Chemicals", 1994, pp. 145-157, vol. 45/46, Publisher: Applied Biochemistry and Biotechnology, Published in: US.

Phillips, J.R., et al, "Mass Transfer and Kinetic Limitations During Synthesis Gas Fermentation by Acetogenic Bacteria", Aug. 7, 2011, Publisher: American Society of Agricultural and Biological Engineers Meeting 2011, Published in: US.

Phillips, J.R., et al, "Method for Design of Production Medium for Fermentation of Synthesis Gas to Ethanol by Acetogenic Bacteria", 2014, pp. 340-346, vol. 7, No. 3, Publisher: Biological Engineering Transactions, Publised in US.

Phillips, John R., et al, "Synthesis Gas As Substrate for the Biological Production of Fuels and Chemicals", Mar. 1, 1994, pp. 145-157, vol. 45, No. 1, Publisher: Applied Biochemistry and Biotechnology, Published in: US abstract only.

Ukpong, et al, "Physiological Response of Clostridium Carboxidivorans During Conversion of Synthesis Gas to Solvents in a Gas-Fed Bioreactor", Jan. 1, 2012, pp. 2720-2728, vol. 109, No. 11, Publisher: Biotechnology and Bioengineering, Published in: US.

Zhang, et al., "Application of a pH Feedback-Controlled Substrate Feeding Method in Lactic Acid Production", May 26, 2010, pp. 2149-2156, vol. 162, Publisher: Appl Biochem Biotechol, Published in: US.

* cited by examiner

SYSTEM AND METHOD FOR FEEDBACK CONTROL OF GAS SUPPLY FOR ETHANOL PRODUCTION VIA SYNGAS FERMENTATION USING PH AS A KEY CONTROL INDICATOR

CROSS REFERENCE TO RELATED APPLICATIONS

This application claims the benefit of U.S. Provisional Patent Application Ser. No. 62/138,080, filed on Mar. 25, 2015, and international patent application number PCT/US2015/060720, filed Nov. 13, 2015, and incorporates said applications by reference into this document as if fully set out at this point.

GOVERNMENT RIGHTS CLAUSE

This invention was made with U.S. Government support under DOT Grant Number DTOS59-07-G-00053 awarded by the Department of Transportation. The Government has certain rights in this invention.

TECHNICAL FIELD

This disclosure relates generally to biofuel production from syngas.

BACKGROUND

Syngas fermentation uses acetogenic bacteria to convert CO and $H_2$ to ethanol, via the Wood Ljungdahl pathway to acetic acid and then reduces the acetic acid to ethanol using electrons and protons derived from $H_2$ or CO. Commercial deployment of syngas fermentation is imminent with INEOS Bio completing construction and start-up of an 8 million gal/yr plant in Vero Beach, Fla., and Lanza Tech constructing large facilities in China. Economics of syngas fermentation require High conversion of both CO and $H_2$ to conserve the energy of the feedstock in the fuel product;

High selectivity of the fermentation to produce ethanol in preference to acetic acid, cell mass or other products; and, High rates of gas consumption and product formation.

Additionally, the fermentation must be stable and capable of long-term continuous operation without interruption and process upset. Control of the syngas supply to match the capacity of the bacterial culture to convert the CO and $H_2$ to ethanol or other products is critical.

Previous research has focused on increasing the rate of mass transfer of CO into the fermentation to overcome the low solubility of CO (and $H_2$) in the aqueous fermentation broth. The prejudice that forced high mass transfer is required (more is better) results in inhibition of $H_2$ uptake by accumulated CO in the cells, reliance on CO as the primary driver of production, and low conversion of $H_2$ with resulting low conservation of energy from the syngas.

Typical control for fermentation processes (without known exception) is based on a choice of an operating pH, and adds base and/or acid to maintain the control set point. This decision requires dedicated pH measurement to control the addition of base from separate equipment, including tanks, mixers, pumps, valves and piping. The addition of base is determined by the effect of fermentation controls operating on the basis of chosen flow and conversion targets. These targets are set for poorly defined (arbitrary) reasons and require continuing assessment and adjustment by the operator.

As such, there is a clear need for an approach that does not suffer the disadvantages of the prior art.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

According to an embodiment, the instant inventors have shown that the objectives of high conversion of both CO and $H_2$ (greater than 95%), with high selectivity for ethanol as a product (greater than 98% of production), recoverable concentrations of ethanol (greater than 19 g/L), in a stable fermentation can be achieved through control of the gas supply and mass transfer applied. This result was achieved in batch fermentation with manual intervention to adjust gas flow and agitation in a continuously stirred tank reactor (CSTR) used as the fermenter. Achievement of these results in this embodiment required frequent (every 2 to 4 hours) sampling, analysis and adjustment of the fermentation.

According to an embodiment, production of alcohols by acetogenic autotrophs is a four electron reduction of organic acid produced in the fermentation; for example, acetic acid is reduced to ethanol. Electrons are supplied by CO and $H_2$ during syngas fermentation. Net production of acid species lowers the pH of the fermentation broth, while the production and accumulation of alcohol does not change pH. Organic acids, particularly acetic acid with $pK_a=4.76$, are produced from CO and $H_2$ taken from the syngas feed, and form an inexpensive buffer with useful strength in the pH range of 4.5 to 5.0. The fermentation broth can be buffered using the organic acids produced during fermentation by the addition of a quantity of base chosen to set a concentration of organic acid salt, for example to convert 1 g/L of acetic acid to acetate. The fermentation pH in this quantitatively buffered broth is a sensitive indicator of net acid production. Fermentation pH can be continuously measured and used with any available process control system to automatically optimize syngas flow to the fermentation to achieve nearly exclusive production of alcohol The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

DETAILED DESCRIPTION

Figure 1:
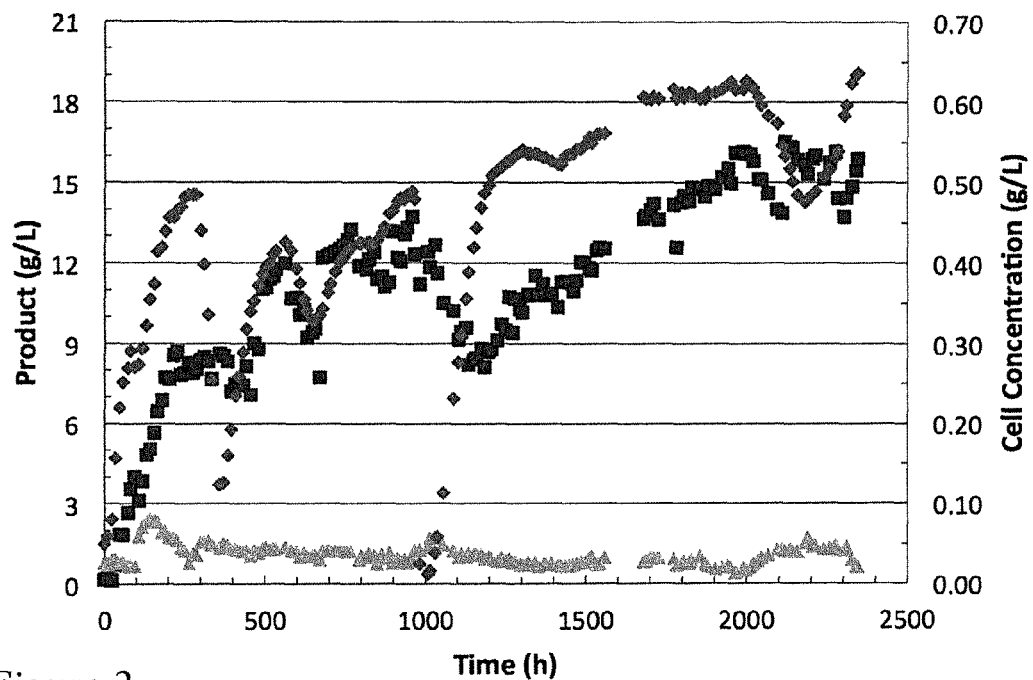
FIG. 1 contains a plot of products of continuous fermentation of syngas mix in the CSTR with feed gas flow adjusted by process control software using a PID (proportional-integral-derivative) control algorithm to maintain pH at set point. Cells (♦), Ethanol (■), Acetate plus acetic acid (▲).

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

Process applications invite optimization. Gas flow and agitation speed can be adjusted to improve the yield, conversion, and rate of gas consumption, or to decrease the cost of production. These changes are inherently destabilizing to the process, and in syngas fermentation can result in an amplified response with loss of culture viability or productivity. Note that additional background information related to various embodiments (including, without limitation, certain mathematical models, additional details related to the fermentation process and its products, alternative methods of optimizing the output of the fermentation process, etc.) can be found in international patent application number PCT/US2015/060720, filed Nov. 13, 2015, the disclosure of which is incorporated by reference as if fully set out at this point.

By way of overview, an embodiment of the invention is founded via the following observations of a syngas fermentation:

One major product of syngas fermentation is acetic acid (an organic acid), the production of acetic acid lowers the pH of the fermentation broth and with added base forms an acetate buffer ($pK_a$=4.75).

Another major product of syngas fermentation is ethanol, which is formed by reduction of the acetic acid with electrons and protons derived from CO or $H_2$ taken from the syngas. Reduction of acetic acid to ethanol raises the pH by consumption of free acetic acid and shifting the equilibrium of the acetate buffer in the fermentation broth.

Consumption of CO and $H_2$ that are converted into the major products acetic acid and ethanol in a fermentation broth with a defined level of buffer (i. e., a chosen acetate concentration) will Lower pH if acetic acid is produced in preference over ethanol;

Raise pH if ethanol is produced in preference over acetic acid; and,

Cause no pH change if production of ethanol matches the production of acetic acid (such that all acetic acid formed in the cell is converted into ethanol) and the acetate buffer in the fermentation broth is not changed.

4 moles of CO and $H_2$ are consumed to produce each mole of acetic acid, and 2 moles of CO and $H_2$ are consumed to convert that mole of acetic acid to ethanol. No net acetic acid is produced or consumed when the amount of CO and $H_2$ supplied and consumed is 50% more than the kinetic capability of the bacterial culture to convert CO and $H_2$ to acetic acid. The formation of acetic acid from syngas is balanced by the conversion of acetic acid to ethanol, at the maximum rate possible for the bacterial culture.

The kinetic capability of the bacterial culture can vary due to changes in nutrient concentrations, gas composition, temperature and pressure, so that an automatic control of gas supply is required to maintain the balance of ethanol and acetic acid production, and stability of the fermentation.

The inhibition of $H_2$ uptake at the hydrogenase enzyme by accumulated CO provides a sensitive indicator of excess mass transfer applied, which is a function of gas flow rate and agitation speed.

Reduction of gas supply to maintain mass transfer limitation in CO supply to the fermentation (marked by near zero concentration of CO inside the cells) avoids CO inhibition of the hydrogenase enzyme and promotes conversion of $H_2$ to products.

According to an embodiment, the measured fermentation pH is a sensitive indicator of optimum syngas supply and can be used to automatically control the rate of feed gas to the fermenter. In one embodiment, the gas supply based on pH control can be accomplished by implementation of:

1. Bias of the controller to reduce gas flow, seeking the lowest gas flow that satisfies the fermentation requirement. This constraint automatically maintains a restricted concentration of CO and provides sustained conversion of $H_2$ and high conservation of both CO and $H_2$ into ethanol, and 2. PID (proportional-integral-derivative) control (an industry standard) of gas flow to maintain conversion of acetic acid to ethanol by reducing the gas flow when pH trends higher (i.e., net acid consumption) and increasing gas flow when pH trends lower (i. e., net acid production). This constraint maintains high selectivity for production of the preferred product ethanol.

3. The intensity of mass transfer ($k_L a/V_L$) is set by fermenter design, such as packing characteristics in a packed column or agitator speed in a continuously stirred tank (CSTR). Mass transfer is applied to achieve economic conversion targets.

Figure 5:
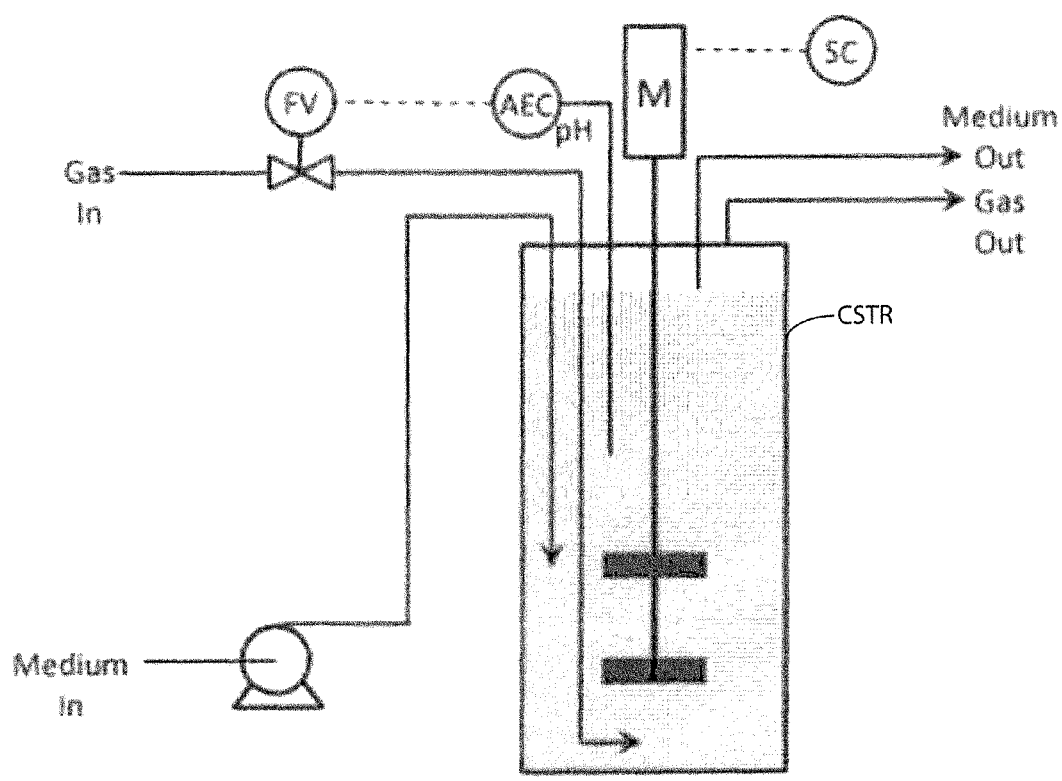
FIG. 5 contains an exemplary configuration of syngas flow controlled to maintain set pH in a CSTR.

A schematic of an embodiment of continuous fermentation and control loops is presented in FIG. 5 for the example of a CSTR. In that figure, the acronym "FV" stands for Flow control Valve, "AEC" is an Analyzer Element Controller, "SC" is a Speed Control for Agitation, and, "M" is a Motor.

INTRODUCTION

Many autotrophic acetogenic microorganisms can produce alcohols and organic acids from CO and $H_2$ found in synthesis gas or syngas (Drake et al., 2008). Alcohols and associated acids produced from syngas include butanol and hexanol (Liou et al., 2005; Liu et al., 2014) and isopropanol from reduction of acetone (Ramachandriya et al., 2011). However, the simple two carbon products acetic acid and ethanol are prominent in syngas fermentation, since they are obtained directly from acetyl coenzyme A (acetyl-CoA) without expense of ATP. Acetyl-CoA is the precursor of all cell carbon and fermentation products in chemoautotrophic growth via the Wood-Ljungdahl pathway (Drake et al., 2008; Phillips et al., 1994). An important step in the production of alcohols is the reduction of the associated acid species through an aldehyde to the alcohol without activation by ATP or Coenzyme A, and requiring four electrons from NAD(P)H (the equivalent of two $H_2$). For simplicity in the discussion that follows, the term acetic acid will be used to generally represent organic acids, acetate of the organic acid salts, and ethanol representative of the associated alcohols. The reduction of acetic acid to ethanol (or other acid/alcohol pair) is an electrochemical couple poised by oxidation/reduction potential (ORP) and pH. ORP is set by the concentration of the substrate gases, CO and $H_2$, acting via the enzymes inside the cells.

Syngas fermentation typically produces a mix of acetic acid and ethanol, with the ratio of products determined by the balance of the kinetic capacity of the bacterial culture and the mass transfer capacity of the fermenter (Phillips et al., 2011). Inhibition of cell activity will result when the supplies of CO and $H_2$ are too high. Slow fermentation and increased acetic acid production will result if mass transfer is limiting. Generally the preferred product is ethanol and accumulation of acetic acid represents a loss of product yield during fermentation. Common practice in fermentation is to maintain pH within a chosen range by the addition of base or acid. In this way a set proportion of the excess acid produced is neutralized and a buffered solution is formed to stabilize pH within the dead band of the on/off controller. Though the pH is stably controlled, gas flow is manually set to a chosen rate, the proportion of gas converted to acetic acid varies and the fermentation may become unstable when supply of CO and $H_2$ is not optimal.

Optimal fermentation of syngas will be achieved when CO and $H_2$ are transferred into the fermentation at the maximum rate of microbial consumption. This balanced fermentation is marked by high activity of the culture and high selectivity for ethanol as the product. Net production of acetic acid lowers pH through release of free protons ($H^+$) and net conversion of acetic acid to ethanol raises pH by consumption of $H^+$.

According to one example, automated control of the syngas flow fed to a continuous fermentation in a continuously stirred tank reactor (CSTR) was used to maintain pH at a chosen operating point within +/−0.001 pH units of the set point. The gas flow was monitored and adjusted by process control software to keep pH in the fermentation broth at the set point with acetate concentration of about 0.5 g/L. This automated control of the syngas feed rate sustained production of ethanol at over 16 g/L.

Methods

In one example, syngas fermentation used *Clostridium ragsdalei* in a standard medium (Gao et al., 2013, the disclosure of which is incorporated by reference herein as if fully set out at this point) with 0.5 g/L yeast extract. The standard medium was modified by omission of the Good's buffer 2-(N-morpholino)ethanesulfonic acid (MES) and the KOH required to charge the buffer. Further, the medium was divided into solution "A" containing 8.40 g/L $NaHCO_3$ and 10 mL/L of a solution containing 4% w/v cysteine and 4% $Na_2S.9H_2O$, and solution "B" containing the minerals, trace metals, vitamins and resazurin solutions.

The medium solutions (1:4 of A:B by volume) were mixed and continuously fed into a 3.0 L Bioflo 110 (New Brunswick Scientific, Edison, N.J.) continuously stirred tank reactor (CSTR) used as the fermenter vessel. The medium was expected to support growth of 0.546 g/L of cell dry weight ($g_x$/L) with growth nutrient limited by Fe (Phillips et al., 2014). The amount of $NaHCO_3$ in the mixed fermentation medium (20.1 mM) was expected to generate 1.2 g/L of acetate from neutralization of acetic acid produced by the bacteria, and generate a buffer to stabilize pH.

Syngas mix containing $H_2$, $N_2$, CO and $CO_2$ (28.5, 5.0, 38.0 and 28.5 mole percent respectively) was fed continuously at a controlled rate through a microsparger, and further dispersed in the fermenter broth by two Rushton impellers (Orgill et al., 2013). Spent gas and liquid exited the fermenter together through a tube arranged to maintain a constant level with about 2450 mL of broth in the fermenter (e.g., as is generally indicated in FIG. 5). Gas samples were taken with a 100 μL syringe (Hamilton, Reno, Nev.) through a septum in the effluent tube and analyzed by gas chromatography. Liquid samples were drawn from a submerged tube, and analyzed for pH, cell concentration as optical density at 660 nm (Cole Parmer, Vernon Hills, Ill.), and then ethanol and acetic acid concentrations were measured by gas chromatography.

The Bioflo 110 instrument console monitors pH via a standard probe (Mettler Toledo, Columbus, Ohio), temperature and agitation speed; temperature was maintained at 37° C., and the agitation speed varied by the operator from the Bioflo 110 console. Feed rates of the liquid media from solutions "A" and "B" were controlled by pump speeds also set on the Bioflo 110 console. The pH was transmitted from the Bioflo 110 to LabView process control software (National Instruments, Austin, Tex.) and a standard proportional-integral-derivative (PID) control algorithm was used to continuously adjust the flow rate of the syngas feed using a thermal conductivity mass flow controller (Porter Instruments, Hatfield, Pa.) such that the pH remained at the chosen set point. Gas flow was reduced through the PID control algorithm if fermenter pH was higher than the set point and increased if pH was lower than the set point.

Results

Figure 2:
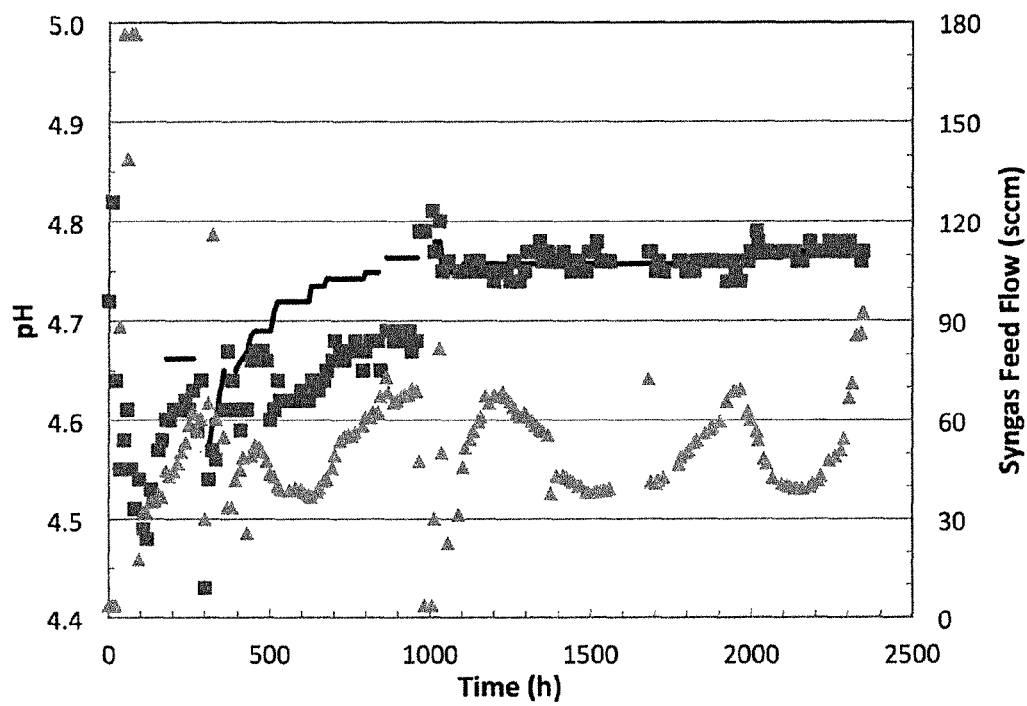
FIG. 2 contains measured pH of liquid samples from continuous fermentation of syngas mix in the CSTR with feed gas flow adjusted by process control software using a PID control algorithm to maintain pH at set point. Set point (–) discontinuous when in manual control, pH (■), syngas flow (▲).

The CSTR ran with continuous gas and liquid flow, and feed gas flow controlled to maintain the fermentation pH at set point for 2345 hours. Products of fermentation, ethanol, acetic acid and cell inventory are shown in FIG. 1 for 2339 hours of operation. The PID control was enabled 142 h after inoculation and automatically maintained fermenter pH near the set point through the remaining period of operation. The acetogenic culture grew and sustained production of ethanol with a small concentration of acetic acid during that period. Ethanol concentration increased to 16 g/L, while acetic acid settled to a steady concentration around 1 g/L. The acetic acid concentration reported includes both free acetic acid produced by the bacteria and the portion neutralized to acetate by the added $NaHCO_3$ in the medium. The acetate and free acetic acid represent the buffer system used to stabilize pH in the fermenter, and at pH 4.75 acetate and free acid are equal ($pK_a$=4.76). The acetate formed after 150 h of operation was about 0.6 g/L and was only half of the 1.2 g/L expected from 20.1 mM $NaHCO_3$ chosen in medium design. Half of the $NaHCO_3$ was expended to neutralize acidic species in the fresh medium. Nonetheless, the buffer formed by $NaHCO_3$ added with the medium "A" effectively stabilized pH as shown in FIG. 2, and enabled maintenance of pH via control of the syngas flow. The pH set point was gradually raised from 4.50 to 4.75 between 150 h and 1000 h, and the concentration of $NaHCO_3$ in medium "A" was increased from 8.4 to 12.6 g/L at 1968 h to strengthen the buffer with higher concentrations of acetic acid plus acetate.

Cell concentration dropped at 262 h and again at 562 h from apparent inhibition as ethanol concentration increased, but the fermentation recovered when the set point for pH was raised. At these times cell growth stopped short of the maximum growth potential achieved later in the experiment. The sudden onset and pH sensitivity of this inhibition suggests substrate (CO) inhibition triggered by accumulating ethanol at low pH.

The sharp drop in cell concentration at 966 h resulted from the operator's effort to increase $H_2$ conversion. Manual control of the gas flow to increase $H_2$ conversion resulted in lower pH, and manual adjustment of pH over-corrected so that the gas flow, which was returned to automatic control, remained low from 969 through 982 h. About 95% of the cell mass collected as a mat at the top of the fermenter vessel, and was removed before the remnant of the culture recovered under the control method over the next 200 hours. The fermentation ran unattended and maintained pH and stable operation from 1570 to 1679 h. The cell concentration at 2340 h is the highest achieved in this medium at about 0.63 g of cells per liter ($g_x$/L). This is double the typical maximum cell mass concentration seen in batch culture.

The set point for pH control was started at about 4.60, raised to 4.62 at 360 h with insertion of a new pH probe, raised again to 4.67 after 625 h, and again to 4.76 after 1030 h. The pH deviated from the set point by up to +/−0.05 when the control was perturbed, but typically settled to highly effective control with deviations of +/−0.001. The controller pH exhibited an offset from the bench reading until the controller span was adjusted to match at 1006 h. The control of pH remained effective when the buffer strength was increased by 50% (30.1 mM $NaHCO_3$) at 1968 h and when the medium flow increased 50% from 0.314 to 0.472 mL/min (130 to 87 h liquid retention time) in a step change at 2286 h.

Figure 3:
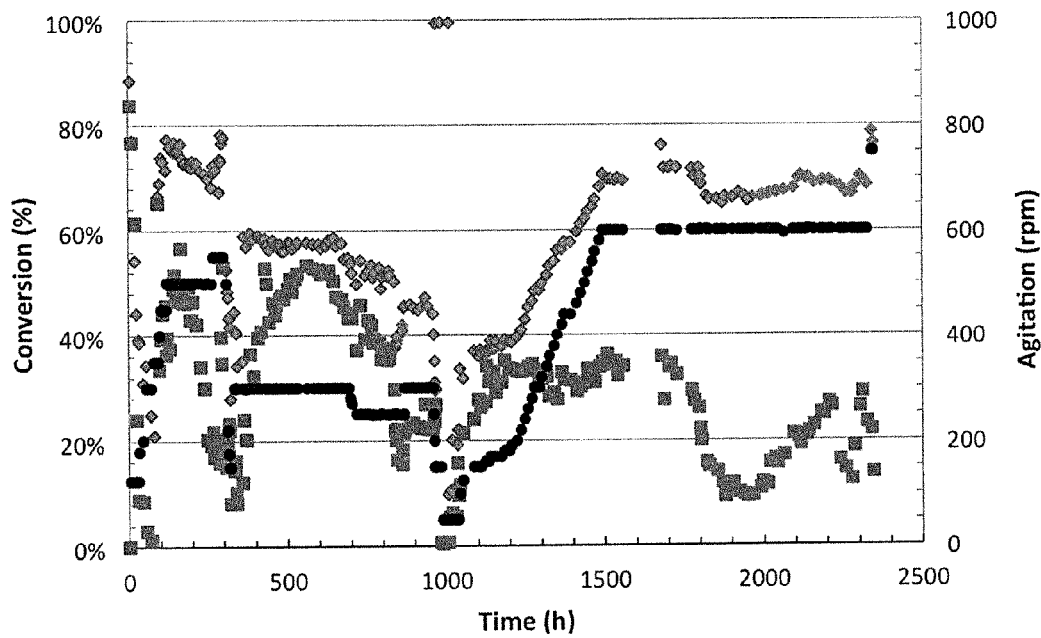
FIG. 3 contains a plot of conversion of substrate gases CO and $H_2$ and agitation speed in continuous fermentation of syngas mix in the CSTR with feed gas flow adjusted by process control software using PID control algorithm to maintain pH at set point. Conversion of CO (♦) and $H_2$ (■), and agitation speed (●).

Two syngas mix compositions were used in this fermentation; a composition of CO (38.0%), $H_2$ (28.5%), $CO_2$ (28.5%) and $N_2$ (5%) was used for the first 102 h, and after 1374 h this mix from the cylinder was diluted with additional $N_2$. A constant $N_2$ flow of 64 sccm was started at 860 h, reduced to 42.5 sccm at 988 h and increased to 68 sccm at 1822 h to dilute $CO_2$ dissolved in the fermentation broth and cells. A mix with CO (30.5%), $H_2$ (29.5%), $CO_2$ (34%) and $N_2$ (6%) was used from 102 h to 838 h and then diluted with $N_2$ from 838 h to 1374 h. The rate of $N_2$ flow was increased by 60% after 1800 h. The conversions of CO and $H_2$ achieved and the agitation speed through the course of this fermentation are shown in FIG. 3.

Figure 4:
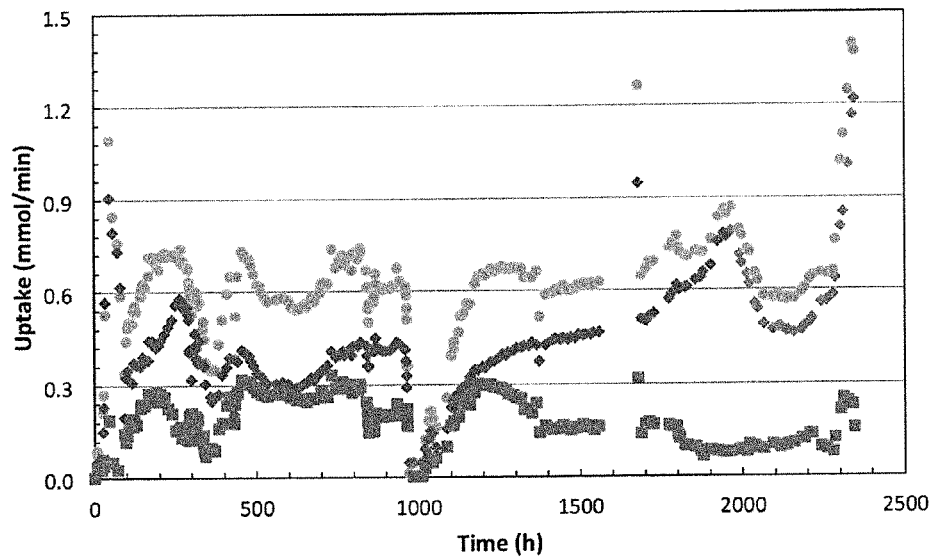
FIG. 4 contains a plot of uptake of substrate gases CO and $H_2$ in continuous fermentation of syngas mix in the CSTR with feed gas flow adjusted by process control software using PID control algorithm to maintain pH at set point. Uptake of CO (♦), $H_2$ (■), and CO+$H_2$ (●).

Growth of C. ragsdalei with concurrent production of ethanol was achieved using CO and $H_2$ together in a single vessel. The agitation speed and thus the power input to achieve mass transfer are relatively low. Conversions greater than 90% for both CO and $H_2$ are targeted to maximize conservation of the energy from the syngas into the ethanol product. Conversion of CO up to 80% is achieved in the early growth of the fermenter, and stable CO conversion of 70% is achieved after 1400 h. Both $H_2$ and CO are converted to over 50% between 500 h and 630 h, showing that ethanol can be produced from either $H_2$ or CO. Conversion of $H_2$ increased as the acetate buffer strength increased after 1968 h, with total uptake falling as less CO was consumed. Conversion of both CO and $H_2$ improved and total uptake increased sharply after medium flow was increased at 2286 h (FIG. 4). Higher gas consumption with sustained cell and ethanol concentrations following an increase in liquid flow indicates that higher productivity can be achieved.

The consumption or uptake of CO and $H_2$ are shown in FIG. 4. The uptake of CO exceeds the uptake of $H_2$ over the course of the fermentation. However, at times the molar consumption of CO and $H_2$ is nearly equal, such as between 400 h and 700 h and again as the fermenter recovers from 1000 h through 1150 h. This shows again that $H_2$ can be used to produce ethanol and maintain the pH using the control method. High conversion of both $H_2$ and CO is required for commercial success of the fermentation, and a goal of this research. The barrier to achieving high conversion of $H_2$ appears to derive from thermodynamic and kinetic considerations imposed when the concentration of dissolved $CO_2$ increases the concentration of dissolved CO. Additional techniques must be developed to achieve high $H_2$ conversion.

In practice an embodiment will operate generally as follows. The sequence of operation is to start the motor for agitation and gas flow (stating at a low value) then continuously monitor pH. If the measured pH is low then increase gas flow; if pH is high then decrease gas flow. The adjustment of gas flow based on the pH can be continued indefinitely during continuous operation until the fermentation is stopped for operational reasons.

Figure 6:
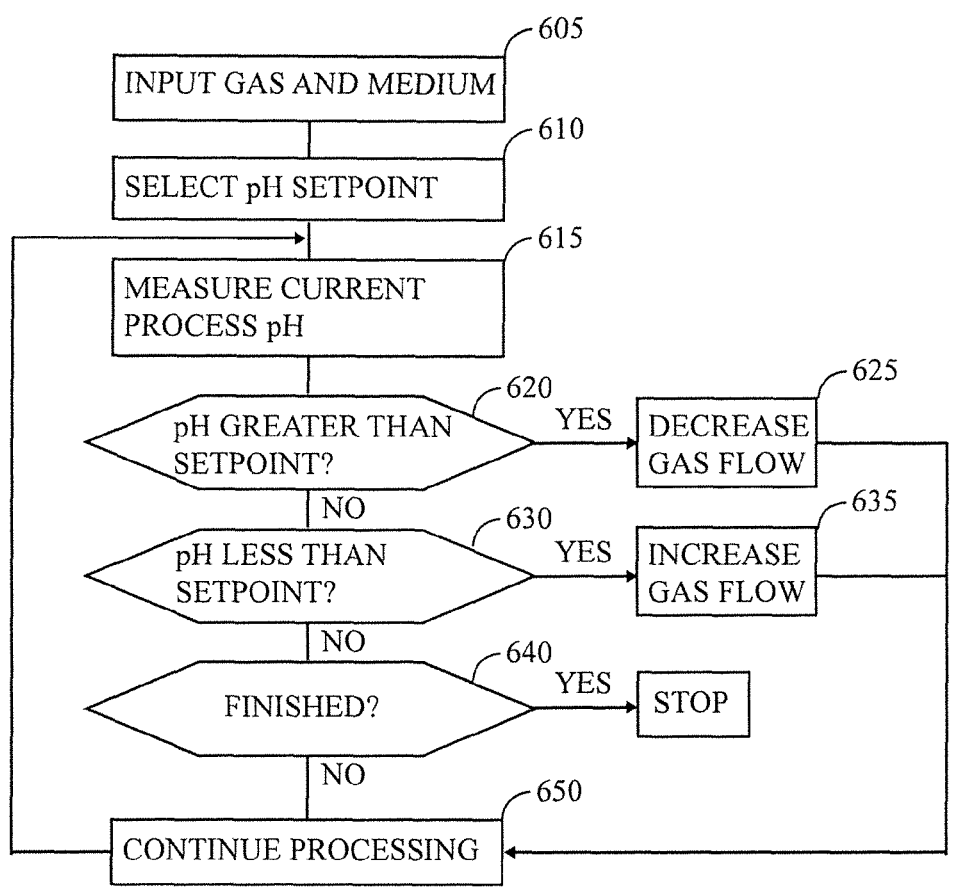
FIG. 6 contains an operating logic suitable for use with an embodiment.

Turning next to FIG. 6, this figure illustrates in greater detail an approach to using pH to control fermentation according to an embodiment. With respect to box 605, one embodiment of the liquid medium would be any growth medium appropriate for the acetogenic bacterial culture. In some embodiments, the medium will be formulated to support a high cell inventory considering cell retention, if used, according to methods well known to those of ordinary skill in the art. This might include a mineral defined medium with essential vitamins, or a rich medium using growth promoters like yeast extract. Medium formulation will affect growth, but is not critical to the control method.

The feed gas might be any gas containing CO and H2 in high enough concentration to support the acetogenic cultures growth and production. This includes, by way of example only, synthesis gas with 70% CO plus H2 or higher, and producer gas with CO plus H2 of 20% or higher. No particular composition or ratio of CO to H2 is required. Additionally, as further examples, gas containing CO, H2, CO2 and CH4 can also be used with the various embodiments disclosed herein.

The medium flow should be as fast as will support the product concentration target which might be chosen based on the available microbial cells in the fermenter; faster liquid flow will wash out the product concentration. Obviously, acceptable flow rates will depend on a number of parameters, including the size and configuration of the CSTR. Medium flow rates in a particular case might be determined empirically by industry rules of thumb, trial and error, etc. Gas flow can be adjusted by the control method taught herein to sustain the product ratio and concentration. Preferred gas and liquid flow rates will be chosen to match the kinetic capability of the microbial culture used.

With respect to box 610 and continuing with the current embodiment, the pH range will be selected to take advantage of the naturally generated acetate buffer with a pKa of 4.75. This will operate best from pH of about 4.75 to 5.0. The culture will grow best at a higher pH, and the buffer is most effective near the pKa of 4.75. An acceptable operating range for this embodiment would be about 4.70 to 5.0.

With respect to box 620, when the measured pH is greater than the pH set point, the controller will decrease the gas flow to the bioreactor. The acceptable offset from the set point pH is not critical, and a variation of +/−0.1 would be acceptable as an example. However, the PID control algorithm will preferably be capable of holding this variation to +/−0.01 pH point. The sensitivity of the pH controller to react depends on the PID set values, which can be changed depending on kinetics of the microbial system used. Typically, the pH controller will react when the difference between the pH set point and the measured value is about 0.01. This difference can be varied to react within a difference of +/−0.1.

Turning next to example of box 625, the control method of this embodiment utilizes a process control method monitored and applied by the control computer without operator intervention.

The control software package of box 625 will be programmed with the functional relationship between gas flow and pH. The process control package should adjust the gas flow very slowly to maintain a stable pH with little offset from the pH set point. Measurements of pH might be read relatively frequency, e.g., 20 seconds or 60 seconds in some cases, although if the process has been stabilized it might be read every five minutes or even less frequently. In some embodiments, the pH might be read every second (or even more frequently). Those of ordinary skill in the art will be able to determine (e.g., on a trial-and-error basis) how often the pH will need to be read in a particular case. Other sorts of controllers and/or associated software could be used with the pH feedback control method. Alternatives would be standard PID control, fuzzy logic or other commercially available process control software.

Considering the example of box 630, when the measured pH is lower than the pH set point, the controller will increase the gas flow to the bioreactor in this embodiment. The acceptable offset from the set point pH is not critical, and a variation of +/−0.1 would be acceptable. However, the PID control algorithm would typically be capable of holding this variation to +/−0.01 pH point. The sensitivity of the pH controller to react depends on the PID set values, which can be changed depending on kinetics of the microbial system used. Typically, the pH controller will react when the difference between pH set point and measured value is 0.01. This difference can be varied to react within a difference of +/−0.1.

Turning next to box 635, an embodiment of the control method depends on use of a process control method monitored and applied by the control computer without operator intervention. The control software package chosen will set the functional relationship for how much gas flow is increased to control the pH at the set point. The process control package will typically adjust the gas flow slowly to maintain a stable pH so that there is little offset from the pH set point. Other controllers can be used with the pH feedback control method. Some suggested alternatives would be standard PID control, fuzzy logic or other commercially available process control software.

In practice and as a specific example, if a sudden change or a disturbance occurred in a bioreactor, such as changes in feed gas composition, agitation speed, liquid medium flow, nutrient deficiency or temperature, etc., the pH controller of an embodiment will react and slowly change the gas flow rate by plus or minus 1% per half hour until the measured process pH returns to the pH set point (i.e., the pH offset is approximately zero). It should be noted that the settings of the PID controller and controller type affect how fast the controller reacts and by how much the gas flow rate is expected to change to bring the pH closer to the set point.

Note that, although CSTR bioreactors have been discussed herein, that was only done to provide a specific example of a bioreactor that would be suitable for use with an embodiment. Those of ordinary skill in the art will recognize that many other types of bioreactors including, without limitation, such as bubble-column, trickle bed, airlift loop, immobilized-cell and membrane bioreactors operated in batch, fed batch, and continuous modes would work as well. As such, when the term "bioreactor" is used herein, that term should be broadly construed to include CSTR bioreactors as well as any other sort of chamber in which a biological reaction or process that uses an acetogenic microbial culture with solventogenic potential to produce fermentation products such as organic acids, alcohols and other chemicals takes place. Collectively, substances that can be produced by an acetogenic microbial culture in a bioreactor will be referred to as fermentation products herein. That being said, syngas conversion is a particular application that would benefit from the methods taught herein.

Successful feedback control of syngas supply for fermentation to produce ethanol is shown herein to use pH as the input variable for a PID controller. The pH of the fermentation broth is a highly sensitive indicator of optimal supply of CO and $H_2$ to syngas fermentation using autotrophic acetogenic microorganisms to produce alcohols, particularly ethanol. A chosen concentration of base, in this case $NaHCO_3$, in the medium converts a small portion of acetic acid produced by the microbes to acetate and forms a buffer of constant strength. All other organic acids are reduced to alcohol using electrons from CO and $H_2$. The inlet gas flow rate is adjusted by standard process control software to maintain constant fermentation pH and the optimal supply of syngas. This is a novel feedback control technique with great potential to stabilize fermentation, sustain high syngas conversion efficiencies with high alcohol yield and minimize production cost.

No known publication provides the control algorithm used to determine the level of gas supply that is taught according to an embodiment herein. Using pH as the control variable for gas flow is valuable in the conversion of syngas to biofuels and chemicals that is on the verge of commercial operations. The embodiments described herein are applicable and effective with any autotrophic acetogenic microbial culture that has solventogenic potential (e.g., production of organic acids, alcohols and other chemicals).

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not to be construed or limited to there being only one of that element unless the context specifically indicates otherwise.

Where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Unless indicated otherwise, methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners☐ of the art to which the invention belongs.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)–(a second number)", this should be interpreted to mean a range of numerical values where the lower limit is the first number and the upper limit is the second number. For example, 25 to 100 should be interpreted to mean a range with a lower limit of 25 and an upper limit of 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

While this invention is susceptible of embodiment in many different forms, there is shown in the drawings, and is herein described in detail, some specific embodiments. It should be understood, however, that the present disclosure is to be considered an exemplification of the principles of the invention and is not intended to limit it to the specific embodiments or algorithms so described. Those of ordinary skill in the art will be able to make various changes and further modifications, apart from those shown or suggested herein, without departing from the spirit of the inventive concept, the scope of which is to be determined by the following claims.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

REFERENCES

Cheng, "Strategy for pH control and pH feedback-controlled substrate feeding for high-level production of L-tryptophan by *Escherichia coli*", World J Microbial Biotechnol (2013) 29:883-890.

Zhang et al., "Application of a pH feedback controlled substrate feeding method in lactic acid production", 2010.

Drake, H. L., A. S. Gossner, and S. L. Daniel. 2008. Old acetogens, new light. In *Incredible Anaerobes: From Physiology to Genomics to Fuels*, 100-128. J. Wiegel, R. J. Maier, and M. W. W. Adams, eds.

Gao, J., H. K. Atiyeh, J. R. Phillips, M. R. Wilkins, and R. L. Huhnke. 2013. Development of low cost medium for ethanol production from syngas by *Clostridium ragsdalei*. *Bioresource Technology* 147(0):508-515.

Liou, J. S.-C., D. L. Balkwill, G. R. Drake, and R. S. Tanner. 2005. *Clostridium carboxidivorans* sp. nov., a solvent-producing *clostridium* isolated from an agricultural settling lagoon, and reclassification of the acetogen *Clostridium scatologenes* strain SL1 as *Clostridium drakei* sp. nov. *International Journal of Systematic and Evolutionary Microbiology* 55(5):2085-2091.

Liu, K., H. K. Atiyeh, B. S. Stevenson, R. S. Tanner, M. R. Wilkins, and R. L. Huhnke. 2014. Mixed culture syngas fermentation and conversion of carboxylic acids into alcohols. *Bioresource Technology* 152:337-346.

Orgill, J. J., H. K. Atiyeh, M. Devarapalli, J. R. Phillips, R. S. Lewis, and R. L. Huhnke. 2013. A comparison of mass transfer coefficients between trickle-bed, hollow fiber membrane and stirred tank reactors. *Bioresource Technology* 133(0):340-346.

Phillips, J. R., H. K. Atiyeh, and R. L. Huhnke. 2014. Method for Design of Production Medium for Fermentation of Synthesis Gas to Ethanol by Acetogenic Bacteria. *Biological Engineering Transactions* 7(3):113-128.

Phillips, J. R., H. K. Atiyeh, R. S. Lewis, and R. L. Huhnke. 2011. Mass transfer and kinetic limitations during synthesis gas fermentation by acetogenic bacteria. In *American Society of Agricultural and Biological Engineers Annual International Meeting* 2011, Aug. 7, 2011-Aug. 10, 2011. Louisville, Ky., United states: American Society of Agricultural and Biological Engineers.

Phillips, J. R., E. C. Clausen, and J. L. Gaddy. 1994. Synthesis Gas as Substrate for the Biological Production of Fuels and Chemicals. *Applied Biochemistry and Biotechnology* 45-6:145-157.

Ramachandriya, K. D., M. R. Wilkins, M. J. M. Delorme, X. Zhu, D. K. Kundiyana, H. K. Atiyeh, and R. L. Huhnke. 2011. Reduction of acetone to isopropanol using producer gas fermenting microbes. *Biotechnology and Bioengineering* 108(10):2330-2338.

What is claimed is:

1. A method of ethanol production via syngas fermentation, comprising the steps of:
   (a) selecting an acetogenic microbial culture with solventogenic potential;
   (b) selecting a pH set point;
   (c) selecting a medium supportive of said acetogenic bacterial culture;
   (d) selecting a feed gas;
   (e) providing said medium to a bioreactor;
   (f) providing a flow of said feed gas to said bioreactor at a predetermined flow rate;
   (g) operating said bioreactor to mix together said feed gas and medium;
   (h) determining a pH of said provided medium and said feed gas within said bioreactor; and using said pH as the measured variable for an automatic control algorithm to adjust the flow of said feed gas such that;
   (i) if said determined pH is greater than said pH set point, reducing said determined pH without adding an acid by decreasing said flow of said feed gas to said bioreactor to a rate lower than said predetermined flow rate at least until the pH of said provided medium and said feed gas within said bioreactor reaches said set point;
   (j) if said determined pH is less than said pH set point, increasing said determined pH without adding a base by increasing said flow of said feed gas to said bioreactor to a rate higher than said predetermined flow rate at least until the pH of said provided medium and said feed gas within said bioreactor reaches said set point; and
   (k) continuing to perform at least steps (f) through (j) until a quantity of said ethanol is produced.

2. The method according to claim 1, wherein step (b) comprises the step of selecting a pH set point around the pKa of the intermediate acid product, for acetic acid to ethanol between 4.7 pH and 5.0 pH.

3. The method according to claim 1, wherein step (i) comprises the step of:
   if said determined pH is greater than said pH set point by more than 0.1 pH unit, reducing said determined pH without adding an acid by decreasing said flow of said feed gas to said bioreactor to a rate lower than said predetermined flow rate at least until the pH of said provided medium and said feed gas within said bioreactor reaches said set point.

4. The method according to claim 1, wherein step (j) comprises the step of,
   if said determined pH is less than said pH set point by more than 0.1 pH unit, increasing said determined pH without adding a base by increasing said flow of said feed gas to said bioreactor to a rate higher than said predetermined flow rate at least until the pH of said provided medium and said feed gas within said bioreactor reaches said set point.

5. The method according to claim 1, wherein said bioreactor is a continuously stirred tank reactor (CSTR) bioreactor.

6. A method of fermentation to produce a fermentation product, comprising the steps of:
   (a) selecting an acetogenic microbial culture with solventogenic potential;
   (b) selecting a pH set point;
   (c) selecting a medium supportive of said acetogenic bacterial culture;
   (d) selecting a feed gas;
   (e) providing said medium to a bioreactor;
   (f) providing a flow of said feed gas to said bioreactor at a predetermined flow rate;
   (g) operating said bioreactor to mix together said feed gas and medium;
   (h) determining a pH of said provided medium and said feed gas within said bioreactor;
   (i) if said determined pH is different from said pH set point, adjusting said determined pH to equal said pH set point without an addition of a base or an acid by changing said flow of said feed gas to said bioreactor to a different flow rate; and
   (j) continuing to perform at least steps (f) through (i) until an acceptable quantity of the fermentation product is produced.

7. The method according to claim 6, wherein step (b) comprises the step of selecting a pH set point between 4.7 pH and 5.0 pH.

8. The method according to claim 6, wherein step (h) comprises the step of: if said determined pH is greater than said pH set point by more than 0.1 pH unit, decreasing said flow of gas to said bioreactor to a rate lower than said predetermined rate.

9. The method according to claim 6, wherein step (i) comprises the step of, if said determined pH is less than said pH set point by more than 0.1 pH unit, increasing said flow of gas to said bioreactor to a rate higher than said predetermined rate.

10. The method according to claim 6, wherein said bioreactor is a CSTR bioreactor.

11. The method according to claim 6, wherein the fermentation product is ethanol.

12. A method of ethanol production via syngas fermentation, comprising the steps of:
    (a) selecting an acetogenic microbial culture with solventogenic potential;
    (b) selecting a pH set point;
    (c) selecting a medium supportive of said acetogenic bacterial culture;
    (d) selecting a feed gas;
    (e) providing said medium to a bioreactor;
    (f) providing a flow of said feed gas to said bioreactor;
    (g) operating said bioreactor to mix together said feed gas and medium;
    (h) determining a pH of said provided medium and said feed gas within said bioreactor;
    (i) if said determined pH is greater than said pH set point, lowering said determined pH to said pH set point without adding an acid by decreasing said flow of said feed gas to said bioreactor;
    (j) if said determined pH is less than said pH set point, increasing said determined pH to said pH set point without adding a base by increasing said flow of said feed gas to said bioreactor; and
    (k) continuing to perform at least steps (f) through (j) until a quantity of said ethanol is produced.

13. The method according to claim 12 wherein step (i) comprises the step of:

(i1) if said determined pH is greater than said pH set point, lowering said determined pH to said pH set point without adding an acid by decreasing said flow of said feed gas to said bioreactor using a proportional-integral-derivative (PID) control algorithm; and, wherein step (j) comprises the step of:

(j1) if said determined pH is less than said pH set point, increasing said determined pH to said pH set point without adding a base by increasing said flow of said feed gas to said bioreactor using a PID control algorithm.

\* \* \* \* \*